(12) United States Patent
Marin

(10) Patent No.: US 10,463,522 B2
(45) Date of Patent: Nov. 5, 2019

(54) DYNAMIC FOOT PLATE

(71) Applicant: MDPO LLC, Sunrise, FL (US)

(72) Inventor: Luis E. Marin, Sunrise, FL (US)

(73) Assignee: MDPO LLC, Sunrise, FL (US)

( * ) Notice: Subject to any disclaimer, the term of this patent is extended or adjusted under 35 U.S.C. 154(b) by 1007 days.

(21) Appl. No.: 14/716,286

(22) Filed: May 19, 2015

(65) Prior Publication Data

US 2015/0282973 A1 Oct. 8, 2015

Related U.S. Application Data

(63) Continuation-in-part of application No. 14/099,177, filed on Dec. 6, 2013.

(60) Provisional application No. 61/782,286, filed on Mar. 14, 2013.

(51) Int. Cl.
*A61F 5/01* (2006.01)
*A61B 17/60* (2006.01)

(52) U.S. Cl.
CPC ............ *A61F 5/0127* (2013.01); *A61B 17/60* (2013.01)

(58) Field of Classification Search
CPC ..................... A61B 17/58–666; A61F 5/0127
USPC ....................................................... 606/53–59
See application file for complete search history.

(56) References Cited

U.S. PATENT DOCUMENTS

| | | |
|---|---|---|
| 2,020,262 A | 11/1935 | Longfellow |
| 2,035,952 A | 3/1936 | Ettinger |
| 2,079,567 A | 5/1937 | Anderson |
| 2,393,831 A | 1/1946 | Stader |
| 2,406,987 A | 9/1946 | Anderson |
| 3,941,123 A | 3/1976 | Volkov et al. |
| 4,176,627 A | 12/1979 | Bassi |
| 4,308,863 A | 1/1982 | Fischer |
| 4,338,927 A | 7/1982 | Volkov et al. |
| 4,535,763 A | 8/1985 | Jaquet |
| 4,607,625 A | 8/1986 | Schenck |
| 4,624,249 A | 11/1986 | Alvarez Cambras |
| 4,696,293 A | 9/1987 | Ciullo |
| 4,768,524 A | 9/1988 | Hardy |
| 5,062,844 A | 11/1991 | Jamison et al. |
| 5,067,954 A | 11/1991 | Ilizarov |
| 5,087,258 A | 2/1992 | Schewior |
| 5,139,498 A | 8/1992 | Astudillo Ley |
| 5,358,504 A | 10/1994 | Paley et al. |

(Continued)

FOREIGN PATENT DOCUMENTS

| | | |
|---|---|---|
| EP | 2194881 | 11/2016 |
| RU | 2391931 C1 | 6/2010 |

(Continued)

*Primary Examiner* — Nicholas J Plionis
(74) *Attorney, Agent, or Firm* — Malloy & Malloy, P.L.

(57) ABSTRACT

A dynamic foot plate assembly structured for therapeutic use adjacent the ankle area of the body comprising a base element, at least one side element extending along the ankle area, and at least one joint movably and adjustably connecting the base element to the side element for variable displacement of the base element and side element into different operative orientations. The dynamic foot plate assembly may also comprise a plurality of strut members disposed in an interconnecting relationship between either a support member and a side element, or the support member and the base element. The strut members, if present, facilitate the variable relative displacement of the base element, side element and support element into different operative orientations.

25 Claims, 12 Drawing Sheets

(56) References Cited

U.S. PATENT DOCUMENTS

| | | |
|---|---|---|
| 5,468,242 A | 11/1995 | Reisberg |
| 5,496,319 A | 3/1996 | Allard et al. |
| 5,540,686 A | 7/1996 | Zippel et al. |
| 5,578,041 A | 11/1996 | Nash et al. |
| 5,681,309 A | 10/1997 | Ross, Jr. et al. |
| 5,702,389 A | 12/1997 | Taylor et al. |
| 5,743,898 A | 4/1998 | Bailey et al. |
| 5,776,132 A | 7/1998 | Blyakher |
| 5,788,695 A | 8/1998 | Richardson |
| 5,814,048 A | 9/1998 | Morgan |
| 5,891,143 A | 4/1999 | Taylor et al. |
| 5,931,837 A | 8/1999 | Marsh et al. |
| 6,030,386 A | 2/2000 | Taylor et al. |
| 6,328,737 B1 | 12/2001 | Moorcroft et al. |
| 6,355,037 B1 | 3/2002 | Crosslin et al. |
| 6,461,358 B1 | 10/2002 | Faccioli et al. |
| 6,964,663 B2 | 11/2005 | Grant et al. |
| 7,025,790 B2 | 4/2006 | Parks et al. |
| 7,048,735 B2 | 5/2006 | Ferrante et al. |
| 7,189,237 B2 | 3/2007 | Huebner |
| 7,361,176 B2 | 4/2008 | Cooper et al. |
| 7,422,593 B2 | 9/2008 | Cresina et al. |
| 7,806,843 B2 | 10/2010 | Marin |
| 7,887,498 B2 | 2/2011 | Marin |
| 8,251,937 B2 | 8/2012 | Marin |
| 8,439,914 B2 | 5/2013 | Ross et al. |
| 2002/0010465 A1 | 1/2002 | Koo et al. |
| 2004/0138659 A1 | 7/2004 | Austin et al. |
| 2004/0167530 A1 | 8/2004 | Hamel |
| 2005/0149018 A1 | 7/2005 | Cooper et al. |
| 2005/0251135 A1 | 11/2005 | Riccione et al. |
| 2007/0055234 A1 | 3/2007 | McGrath et al. |
| 2007/0161984 A1 | 7/2007 | Cresina et al. |
| 2007/0255280 A1 | 11/2007 | Austin et al. |
| 2009/0082709 A1 | 3/2009 | Marin |
| 2009/0105621 A1 | 4/2009 | Boyd et al. |
| 2009/0177197 A1 | 7/2009 | Marin |
| 2009/0275944 A1 | 11/2009 | Huebner et al. |
| 2010/0179548 A1 | 7/2010 | Marin |
| 2010/0234844 A1 | 9/2010 | Edelhauser et al. |
| 2010/0234896 A1 | 9/2010 | Lorenz et al. |
| 2012/0209163 A1 | 8/2012 | Phillips |
| 2012/0330312 A1 | 12/2012 | Burgherr et al. |
| 2014/0257287 A1 | 9/2014 | Chang et al. |
| 2014/0276260 A1 | 9/2014 | Marin |
| 2015/0032107 A1 | 1/2015 | Marin |
| 2015/0282973 A1 | 10/2015 | Marin |

FOREIGN PATENT DOCUMENTS

| | | |
|---|---|---|
| WO | WO 2007/067297 | 6/2007 |
| WO | WO2007111576 A2 | 10/2007 |
| WO | WO 2009/042167 | 4/2009 |
| WO | WO 2010/083033 | 7/2010 |
| WO | WO 2014/152559 | 9/2014 |
| WO | 2016196498 A1 | 12/2016 |

DYNAMIC FOOT PLATE

CLAIM OF PRIORITY

The present application is a continuation-in-part application of U.S. patent application Ser. No. 14/099,177, filed on Dec. 6, 2013 which also claims priority under 35 U.S.C. § 119(e) to a provisional patent application filed with the U.S. Patent Office on Mar. 14, 2013, and assigned Ser. No. 61/782,286, incorporated herein by reference.

BACKGROUND OF THE INVENTION

Field of the Invention

This invention is directed to a support assembly for use in operative placement relative to and treatment of the ankle area including the ankle joint, foot and correspondingly disposed lower leg bones. The assembly allows for a variable orientation of at least one of its members, at least one of which is structured for the disposition of at least one transfixion pin for the engagement and treatment of a patient's ankle area.

Description of the Related Art

In the medical treatment of pathologies including, but not limited to, injuries, fractures, etc. to the bone and joints, external fixator assemblies are commonly used to maintain segments of the bone in an intended and/or required stabilized orientation. By way of example, fixator assemblies of the type described may be utilized to treat the fusion of bone tissue as well soft tissue injuries, and situations involving a union of bones which otherwise are difficult to heal. As such, known or conventional fixator assemblies vary in structure, dimension and configuration and are correspondingly adapted to be used with various portions of the body to which they are attached.

Typical fixator structures include at least one connecting bar or rod as well a plurality of clamps for adjustably securing fixation pins, wires, etc. to the bone portions being affected. Further, transfixion pins or wires of the types commonly utilized may extend completely through the bony tissue or may be anchored therein, such as when the long bones of the leg are involved directly or indirectly with the treatment or healing procedure. Further, the term "transfixion member" is generally recognized in the medical field as including the describing of elongated pins which extend completely or at least partially through the bony tissue involved. In contrast, smaller, thicker "half pins" may be utilized in substantially the same manner to stabilize affected tissue but being of a length insufficient to extend completely through the affected bone, joint, etc. This term may also be used in a more generic sense in referring to stabilizing devices, other than pins, such as wires, reduction wires, screws, clamps, etc.

In addition, known external fixator assemblies of the type described may also include support rings which encircle a corresponding body member, wherein such rings or like support elements serve as a supportive base to facilitate proper location of the aforementioned transfixion members. Accordingly, it is commonly understood in the medical profession that fixator assemblies are used to maintain proper orientation of one or more of bones or bone segments relative to one another to facilitate healing or alignment.

However, the proper stabilization of tissue typically associated with the joint areas of a patient's body such as, but not limited to, the ankle joint as well as the wrist and other smaller bones associated with the hand involves additional considerations.

It would therefore be beneficial to implement a technology that incorporates dynamic aspects to allow for the acute and/or gradual relocation of a foot, ankle or leg deformity. With the dynamic properties of the assembly, a foot, ankle or leg soft tissue and bony pathology can be corrected. In addition, the calibration of the movable components of the assembly allows for ease of use and increased accuracy of adjustments, allowing the surgeon to correct complicated deformities.

SUMMARY OF THE INVENTION

This invention is directed to a dynamic foot plate assembly primarily, but not exclusively, structured for placement adjacent an ankle area of the body. As referred to herein, the term "ankle area" is intended to describe the ankle joint, as well as bones and associated tissue of the foot and lower portions of the leg including the fibula and tibia. Further, in properly describing the intended position and orientation of the various preferred embodiments of the external fixator assembly of the present invention, terminology including "length of the ankle area" and/or "height of the ankle area" may be utilized synonymously. These terms are meant to refer to the general distance between the bottom of the foot and an area of the lower part of the leg above the ankle joint. Further the ankle area, as used herein, is meant to be descriptive of the bones and other tissue associated with the foot, ankle joint and lower leg which serve to facilitate the functioning of the ankle joint and intended, relative movements of the corresponding foot and leg connected to the ankle joint.

Accordingly, the dynamic foot plate assembly includes a configuration of side elements and joints connected to a base element intended to be disposed adjacent to the ankle area. The side elements are structured to support at least one transfixion pin or like transfixion member in operative engagement with the bones or other associated tissue of the ankle area. Consequently, the assembly includes at least one base segment preferably, but not necessarily, having a curvilinear configuration substantially in the form of an arc and or/semi-circle operatively disposed at the medial and lateral longitudinal segments.

In addition, the assembly includes a configuration of joints and side elements attached to the base element and extending transversely from the base element and adjacent the ankle area. The joints and side elements are movably connected and structured to allow variable disposition of the side elements relative to the base element, including but not limited to rotation, raising/lowering, hinging/tilting, and varying the longitudinal spacing/telescoping of the configuration. Some joints may be further capable of being locked or fixed, allowing for the configuration of joints and side elements to become fixed relative to one another. Joints can subsequently be unlocked, restoring the ability for the configuration to once again be articulated.

Further, at least one strut member, which may work in concert with at least one joint, extends from a support member, disposed adjacent the ankle and above the base element, and can be connected to either a base element or a side element to allow for the relative disposition of the dynamic foot plate array into a desired orientation for treatment.

One embodiment of the present invention comprises a base element, as previously described, movably interconnected to two joints, each disposed on an opposing side of the ankle, which are in turn movably interconnected to a pair of side elements extending substantially transversely to the base along opposing sides of the ankle. A pair of strut members are structured to movably interconnect the base element to a support member disposed adjacent to the ankle. A second pair of strut members are structured to movably interconnect the support member to the aforementioned side elements. The four strut members and two joints are structured to cooperatively dispose the base element, side elements and support member into a desired orientation for treatment of the ankle and related areas of the lower leg.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 9:
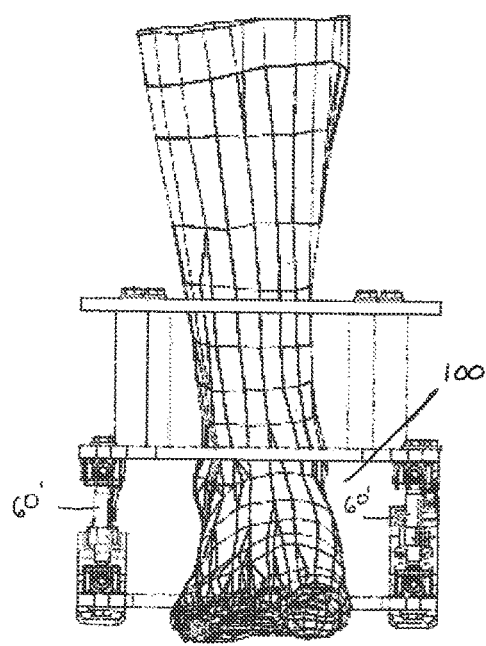
FIG. 9 is a front view of another preferred embodiment of the present invention when operatively positioned relative to an ankle area of a patient.
Figure 10:
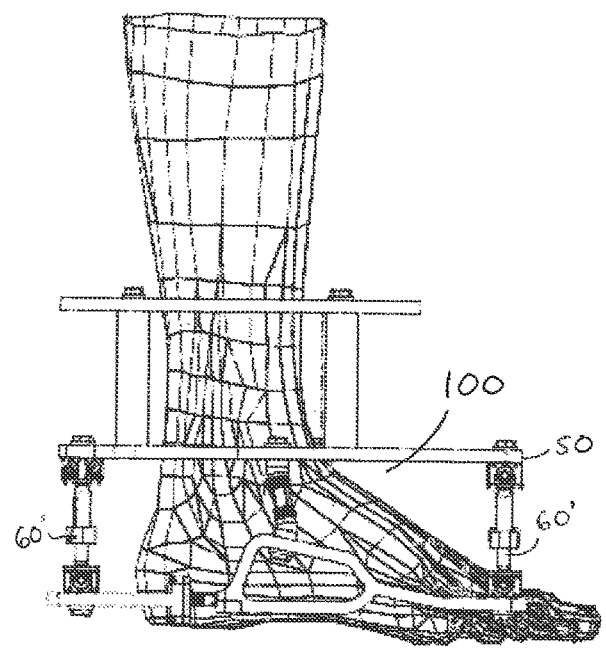
FIG. 10 is a side view of the embodiment of FIG. 9 when operatively positioned relative to an ankle area of a patient.

As represented in the accompanying figures, the present invention is directed to a dynamic foot plate assembly generally indicated as 1. As demonstrated the dynamic foot plate assembly 1 is structured to be operatively positioned and used in a location substantially adjacent the ankle area 100 of a patient as indicated in FIGS. 9 and 10. As set forth above, the ankle area 100 is meant to be descriptive of substantially the entire area, which includes the ankle joint, foot, corresponding portions of the leg bones, including the fibula and tibia, as well as the associated components and tissue. In addition, the terms "height" and "length" of the ankle area 100 are used synonymously herein and refer to the distance from substantially the bottom of the foot, to at least a portion of the long bones of the leg.

Figure 6:
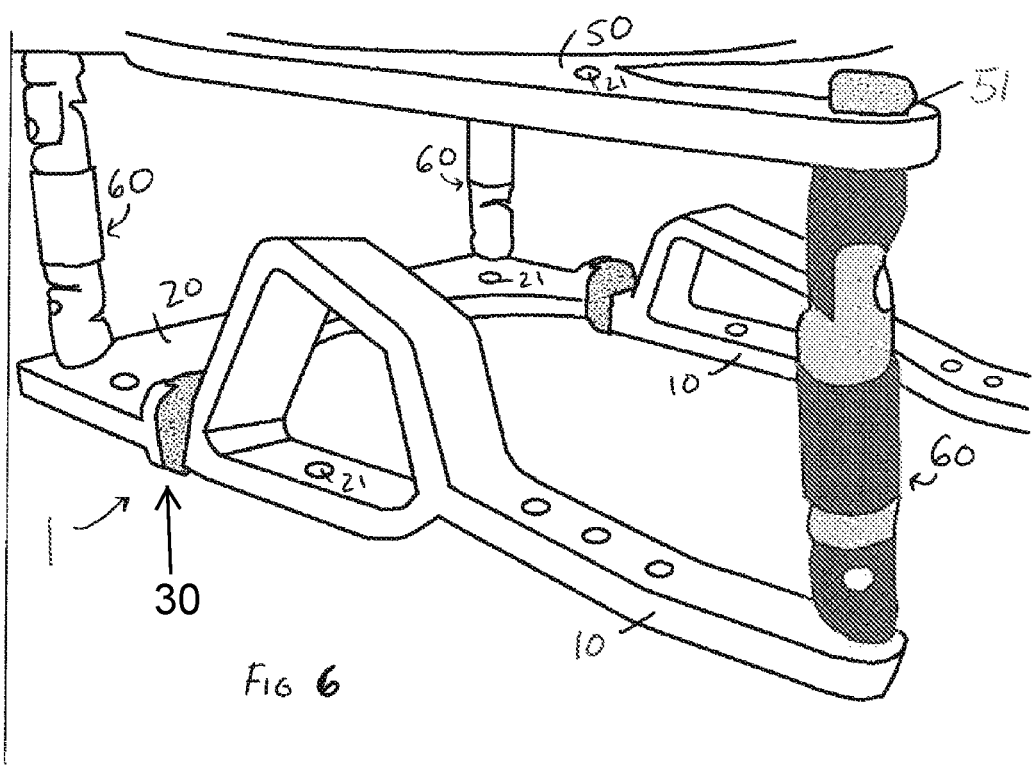
FIG. 6 is a side perspective view in partial cutaway of a plurality of strut members which may be operatively associated with the preferred embodiment of FIG. 1.
Figure 11:
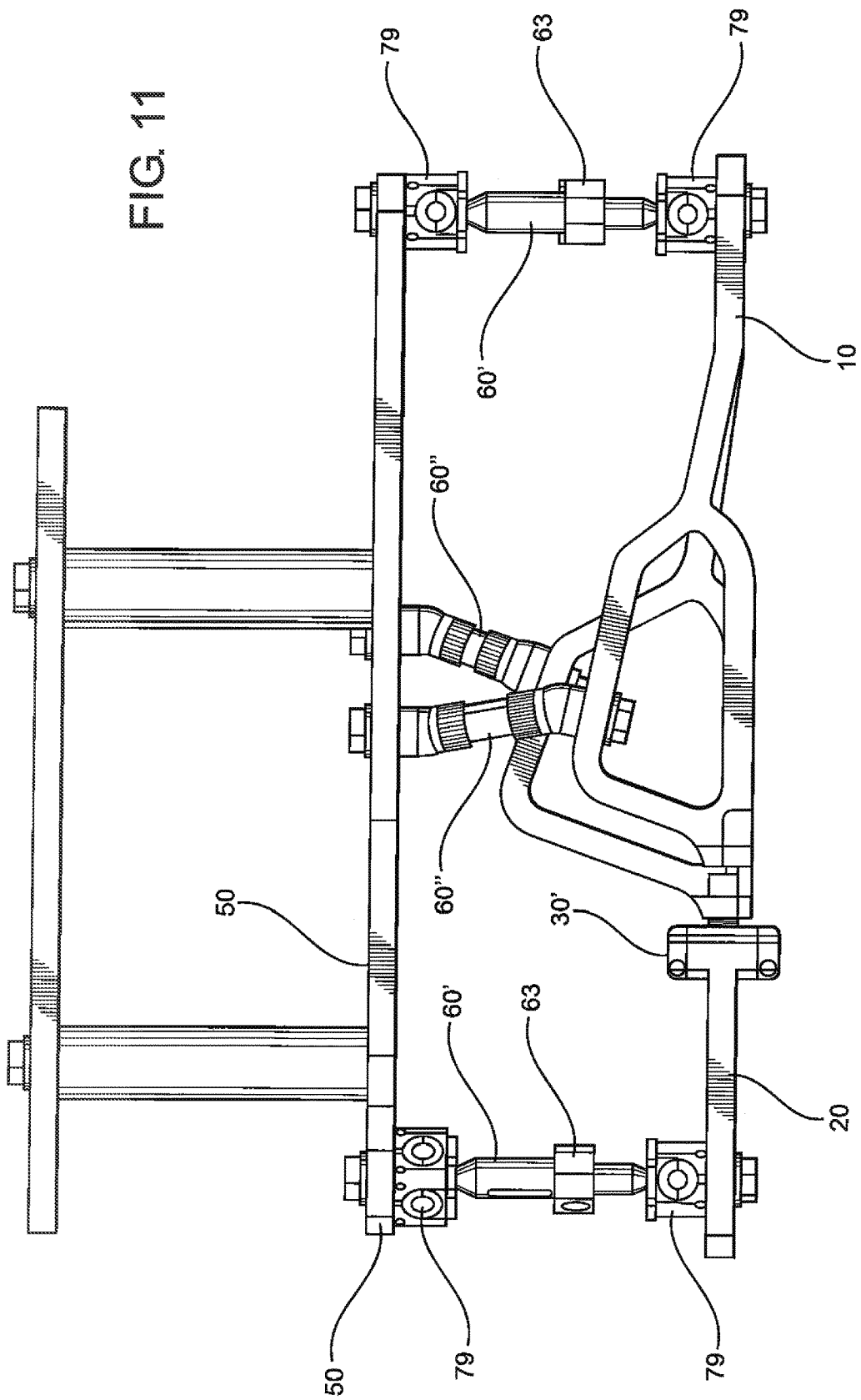
FIG. 11 is a side view of the embodiment of FIG. 9.

Accordingly, the dynamic foot plate assembly 1 comprises a base element generally indicated as 20 movably interconnected to at least one joint generally indicated as 30. In FIG. 11, a possible alternate embodiment of a joint is given at 30'. With reference to FIG. 6, additionally, the foot plate assembly 1 further comprises at least one strut member generally indicated as 60 interconnected to at least one support member generally indicated as 50 and at least one side element generally indicated as 10. With primary reference to FIG. 1, the base element 20 defining at least a portion of the dynamic foot plate assembly 1 in the preferred embodiment includes a curvilinear configuration which may be more specifically defined by an arcuate or semi-circular shape, but other suitable shapes will suffice. As such, the base element 20 terminates in oppositely disposed free ends 22. Further, a plurality of apertures 21 or other appropriate structure are positioned substantially along the length of the base element 20, at least one side element 10, and the support member 50, and are provided to facilitate connection of at least one fixation strut preferably using fixation bolts, which are not shown for purposes of clarity. Such struts and interconnecting fixation bolts are used to support and/or dispose the base segment 20 in a stabilized position relative to the ankle area 100. The opposite ends of such struts, to which the base element 20 is connected, may be secured to a halo-type ring located above the ankle area 100 along the length of the leg and in surrounding relations to the bones of the leg. Such anchoring of the halo ring provides stabilizing support to the base element 20 by virtue of the interconnection between the halo ring and the base element 20 by the plurality of strut members 60.

Figure 1:
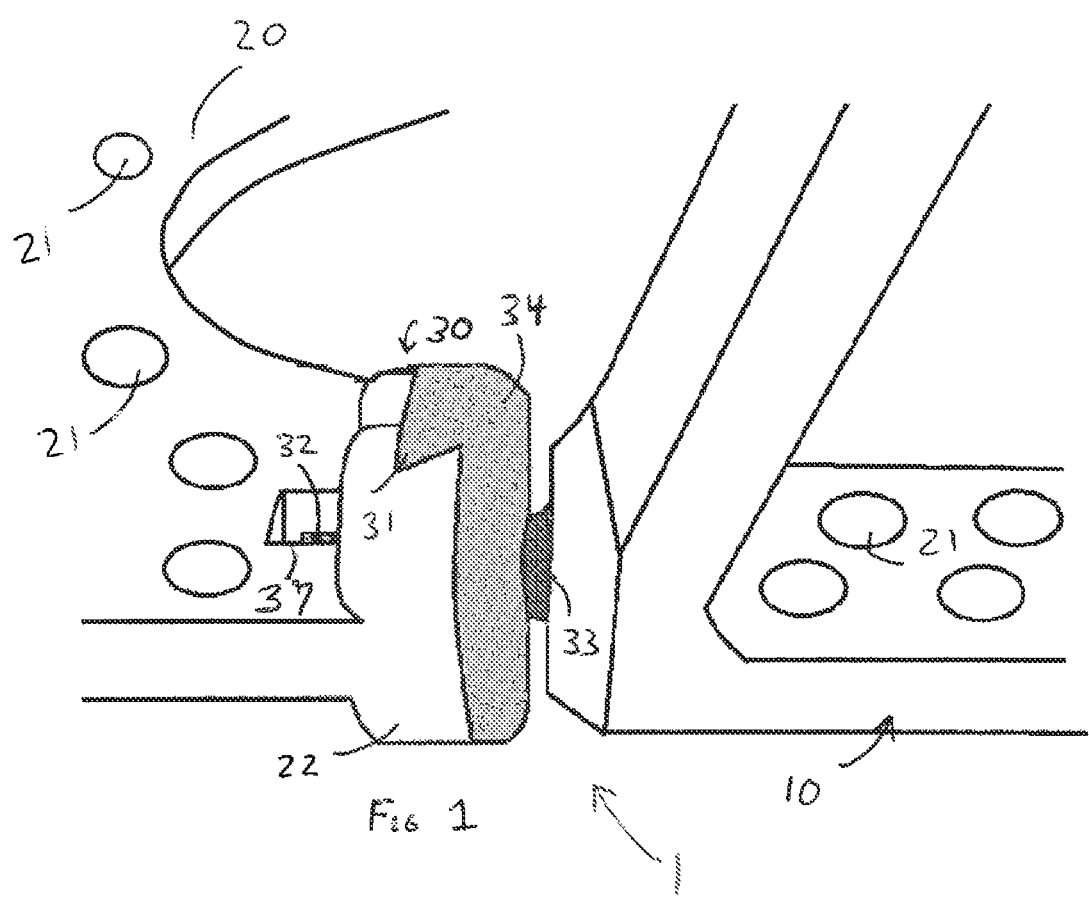
FIG. 1 is a side perspective view in partial cutaway of one preferred embodiment of the present invention.
Figure 2:
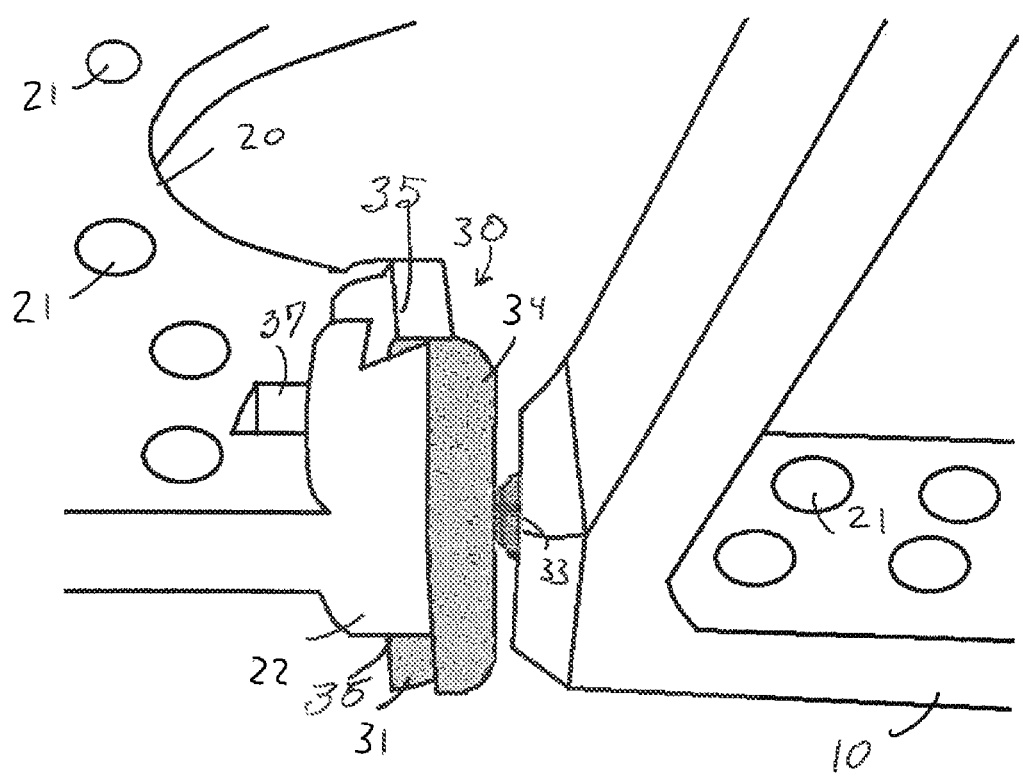
FIG. 2 is a side perspective view in partial cutaway of the joint of the preferred embodiment of FIG. 1.
Figure 3:
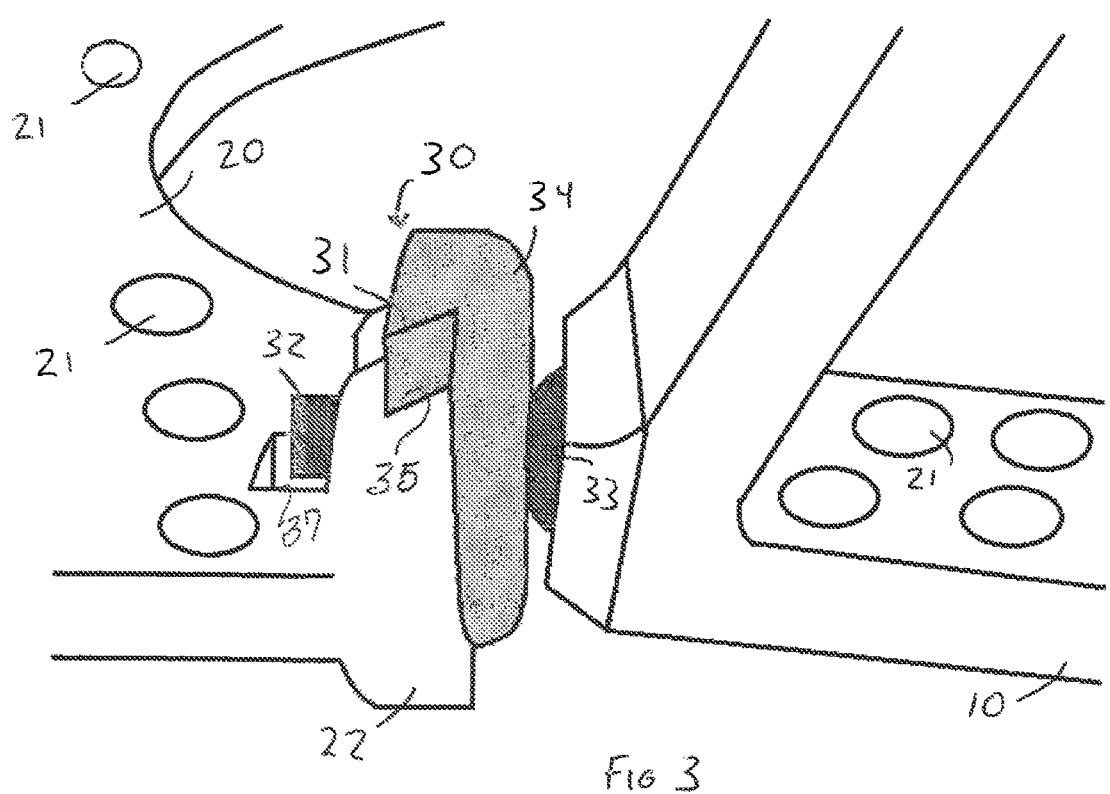
FIG. 3 is a side perspective view in partial cutaway of the joint of the preferred embodiment of FIG. 1.

With primary reference to FIG. 1, the joint 30 as depicted in the preferred embodiment comprises a joint housing 34, an extension element 32, and a pivot element 33. The joint housing 34 can be made of any sufficiently rigid or sturdy material, such as in the depicted embodiment and is preferably centrally apertured to receive the extension element 32, which extends substantially into and, in this case, through the joint housing 34, into an aperture 37 formed in or adjacent to the end 22 of the base 20. In other embodiments, the extension element 32 may only partially recess into the joint housing 34. The joint housing 34, in at least one of the preferred embodiments, may be curvilinear about its circumference, but other suitable geometric configurations will suffice. The joint housing 34 also includes at least one flange 31 extending outwardly in a direction substantially transverse and/or perpendicular to a remainder of the joint housing 34. In addition, the one or more flanges may have an elongated configuration extending at least partially along the height or length of the remainder of the flange housing 34 so as to be disposed adjacent and/or contiguous opposite ends of the flange housing 34, as represented in at least FIGS. 2-5. The flanges facilitate a confronting movable and/or sliding engagement with an adjoining structure which, in the depicted embodiment is the corresponding one of the cooperatively configured and structured ends 22 of the base element 20. However, in at least one alternative embodiment the joint housing 34 and flange 31 may be movably and/or adjustably connected to another part of the dynamic foot plate assembly 1, such as a cooperatively disposed, dimensioned and structured portion and/or corresponding end of the side element 10. The flanges 31 maintain interconnection between the joint housing 34 and the base element 20 while simultaneously facilitating linear movement substantially resembling sliding in the direction of the length and/or height of the of the flanges 31, as depicted in FIGS. 2-5. This sliding, or "vertical" displacement, confers a significant benefit to a medical professional using the dynamic foot plate assembly 1 by allowing the adjustment of the various components of the dynamic foot plate assembly 1 into a desired orientation by varying the disposition of the base element 20 relative to at least one side element 10 both prior to the onset of and during treatment.

Accordingly, the extension element 32 may be a substantially elongated member that extends wholly or substantially through a correspondingly disposed and configured opening or aperture 37 in the end 22 of the base 20. In addition, the extension element 32 extends through and is transversely aligned with the opening 37 and length of the flange 31 into the joint housing 34. The length and dimension of the extension element 32 may resemble a screw, bolt or other threaded rod-like structure capable of extension through or partially through the joint housing 34. The extension element 32 in the preferred embodiment is a threaded elongated member, with the threads extending substantially along the outer length of the extension element 32 and facilitating a frictional confronting and/or threaded engagement with opposing threads lining the interior of the central aperture in the joint housing 34. Therefore, the extension element 32 and the joint housing 34, being interconnected, may reciprocally move transversely to the plane of the base 20. Further, due to the fact that the extension element 32 is connected to the pivot element 33, the one side element 10 also may be selectively disposed relative to the plane of the base 20 such as being raised above the base 20 or disposed below the base 20, relative to the ankle area 100 when the dynamic foot plate assembly 1 is operatively disposed relative to the ankle area 100.

The structure of the extension element 32 allows for the variable disposition or displacement of the base element 20 and at least one side element 10, or alternatively between two side elements 10, directed along the length of the joint housing 34. This is depicted in at least FIGS. 3-5. Variable disposition is achieved by rotation of the extension element 32 about its axis, which can extend or retract the extension element 32 through the joint housing 34, flange 31 and possibly into the aperture 37, via the utilization of the threads extending substantially along the length of the extension element 32. Further, operative positioning of the extension member 32 will be explained in greater detail with regard to the embodiment of FIG. 13.

Figure 4:
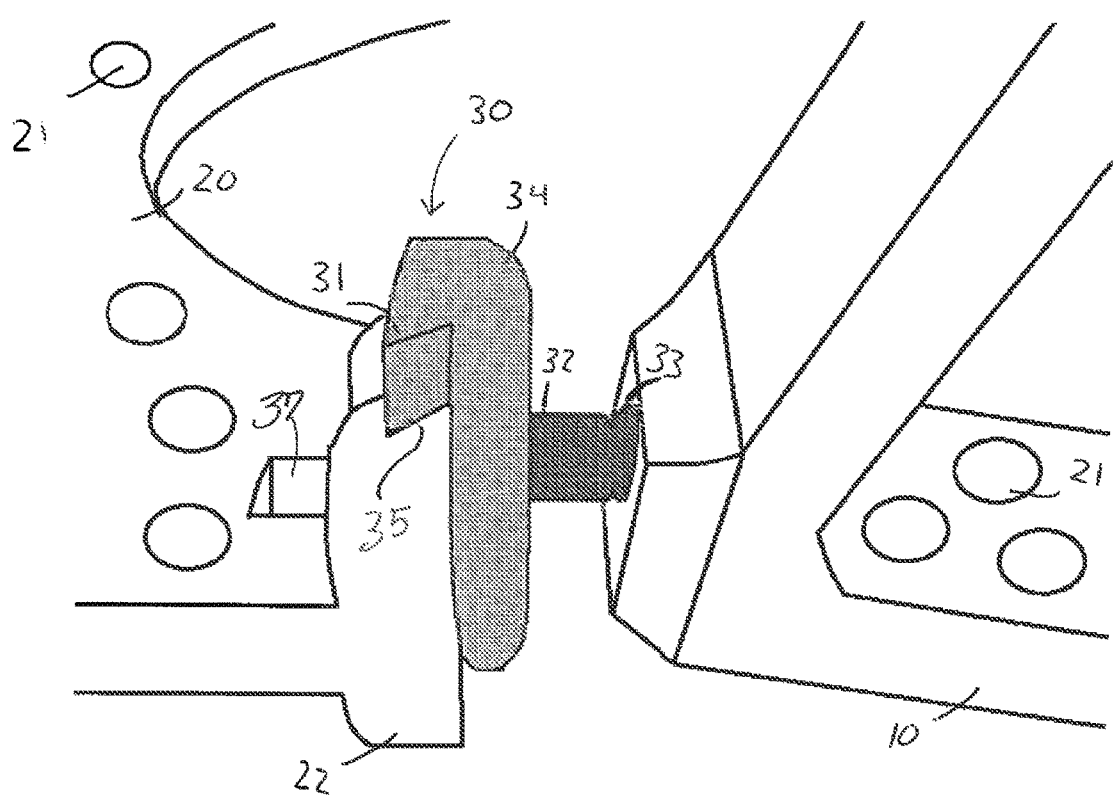
FIG. 4 is a side perspective view in partial cutaway of the joint of the preferred embodiment of FIG. 1.
Figure 5:
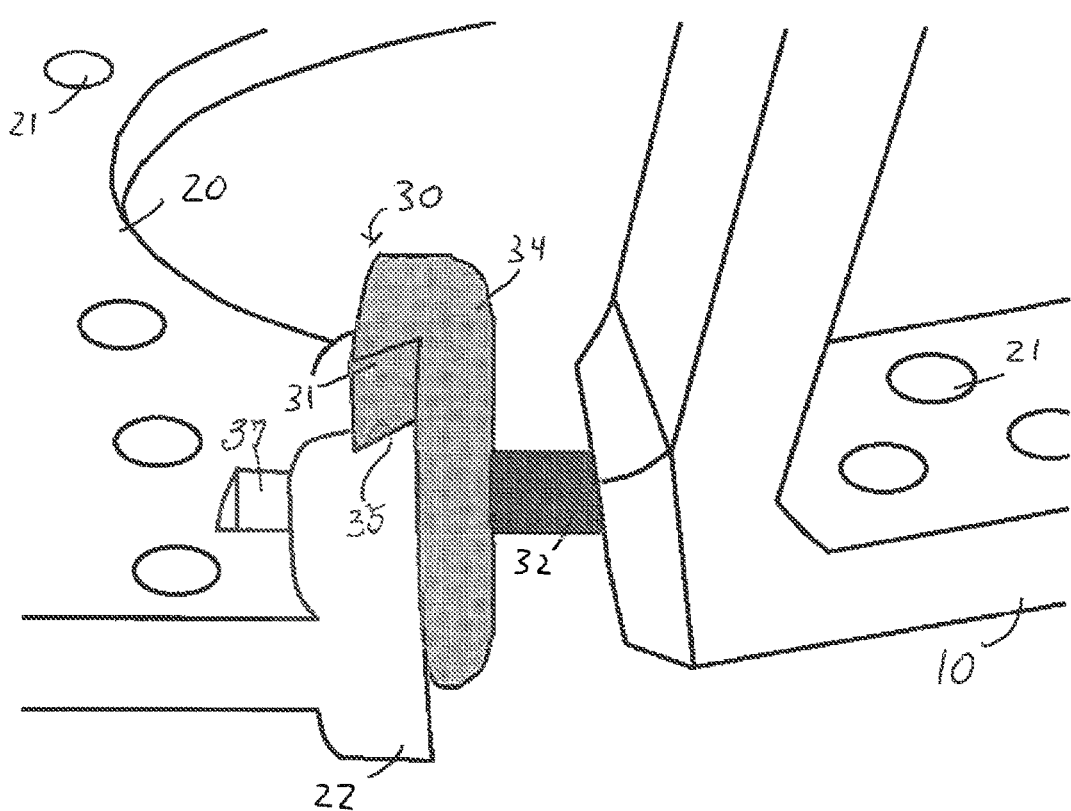
FIG. 5 is a side perspective view in partial cutaway of the joint of the preferred embodiment of FIG. 1.

Attached to the extension element 32 preferably, but not necessarily, at one end of the extension element 32, is a pivot element 33 structured for an at least partially universal range of motion. The pivot element 33 may comprise a ball and socket or substantially equivalent structure. The pivot element 33 facilitates a tilting or angularly oriented movement to establish a preferred or predetermined variance of the angular disposition of the axis or length of the side element 10 relative to the base element 10 as depicted in FIGS. 4 and 5. Alternatively, in another embodiment, the joint 30 could be configured to connect two side elements 10, allowing for a similar tilting motion by way of the pivot element 33, disposed in a socket in one of the two side elements 10, to vary the angular disposition of the axes between the two side elements 10. The pivot element 33 also facilitates the relative varying of the disposition of a base element 20 and a side element 10, as shown in the preferred embodiment, or between two side elements 10, in a lateral direction toward or away from the ankle. Finally, the joint 30 may also facilitate a rotational or rotary movement in such a way that does not vary the angular disposition of the base element 20 and side element 10, or as between two side elements 10. Further, the structural and operative features of the joint 30 and its cooperative components comprise movements of a side element 10 with either a base element 20 or another side element 10, being facilitated by the pivot element 33. Such movements can be a compound movement that includes at least one of the aforementioned tilting, lateral, and/or rotary movements, necessary for a medical professional or other operator to properly dispose a side element 10 into a predetermined orientation relative to the ankle area 100 and base 20 to effect treatment.

Accordingly, the joint 30 including the extension member 32 and pivot member 33, when assuming the structural and operational features as represented in at least FIGS. 1-5 and/or equivalent structure is capable of a variety of different movements and positions being assumed between the base 20 and a corresponding one of the side elements 10. More specifically, the adjustably interconnected side element 10 may move rotationally about the longitudinal axis of the extension member 32; may move angularly upwardly, downwardly, inwardly, outwardly, relative to the ankle area 100 enclosed by the dynamic footplate 1. In addition, the joint 30, including the joint housing 34 and flange 31 may be disposed, as represented in FIGS. 1-5, either upwardly, or downwardly or insubstantial alignment with the plane of the base 20 as represented in FIG. 1. Further, the provision of the extension member 32 within the joint 30 facilitates a variance in the spacing between (inwardly towards or outwardly away from) the base 20 and/or corresponding end 22 thereof and an end portion of the corresponding side element.

Figure 13:
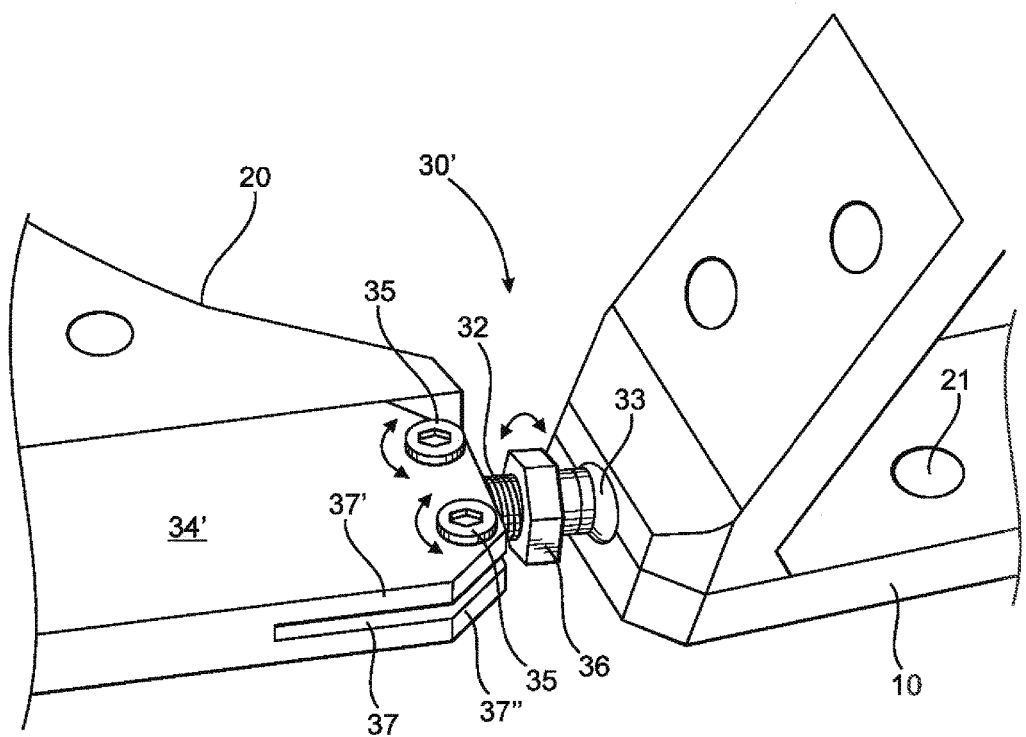
FIG. 13 is a perspective view in partial cutaway of one of a plurality of joints as structured in at least one preferred embodiment of the present invention.

Another embodiment of the joint is given at 30' as shown in FIG. 13. This embodiment may further comprise a nut 36 or similar centrally apertured connector type structure disposed upon the extension element 32 and coaxially aligned therewith. The nut 36 is capable of translation along the extension element 32 and can be placed in confronting engagement with the side element 10. This confronting engagement between the nut 36 and the side element 10 restricts or eliminates the movement of the side element 10 facilitated by the pivot element 33 as described above. Additionally, the joint 30' may comprise an alternate embodiment of a joint housing 34' interconnected to a base element 20 or side element 10. This joint housing 34' may comprise a plurality of bolts, nuts, or other connector or compression elements, represented as 35. These connector or compression elements 35 may be threaded such that a rotational force, such as with a screwdriver, hex key, wrench, etc. is applied about the central axis, the head of any one of the compression elements 35 exerts a compressive force upon the joint housing 34'. The result of the compressive force is to increase the frictional forces exerted upon the extension element 32, causing the extension element 32 to become frictionally locked in a desired orientation. Consequently, the joint housing 34' may be structured in such a way that the frictional force component of the frictional confronting engagement, as previously described, exerted upon the extension element 32 by the joint housing 34' is capable of being varied. One of a possible number of structures is the inclusion of an aperture or gap 37 or similar spacing between two separate parts 37', 37" of the joint housing 34', in which the extension element 32 is disposed. As such, a compressive force exerted by a compression element 35 causes the aperture or gap 37 to decrease in width, resulting in the substantially fixed "clamping" of the extension element 32 there between. Consequently, the two parts 37', 37" of the joint housing 34' are forced together, and in turn increase the compression and thus frictional forces, i.e. clamping forces, exerted upon the extension element 32. Thus, the extension element 32 is sandwiched between the two parts 37', 37", causing the extension element 32 to become frictionally locked or clamped in a desired orientation, which may limit the outward extension or positioning of the extension element and the spacing between the side element 10 and the joint housing 34'. Rotating the compression element or elements 35 in the opposite direction causes the gap 37 to widen, decreasing the aforementioned clamping forces and unlocking the compression element 32, restoring its capability for previously described movement.

Figure 7:
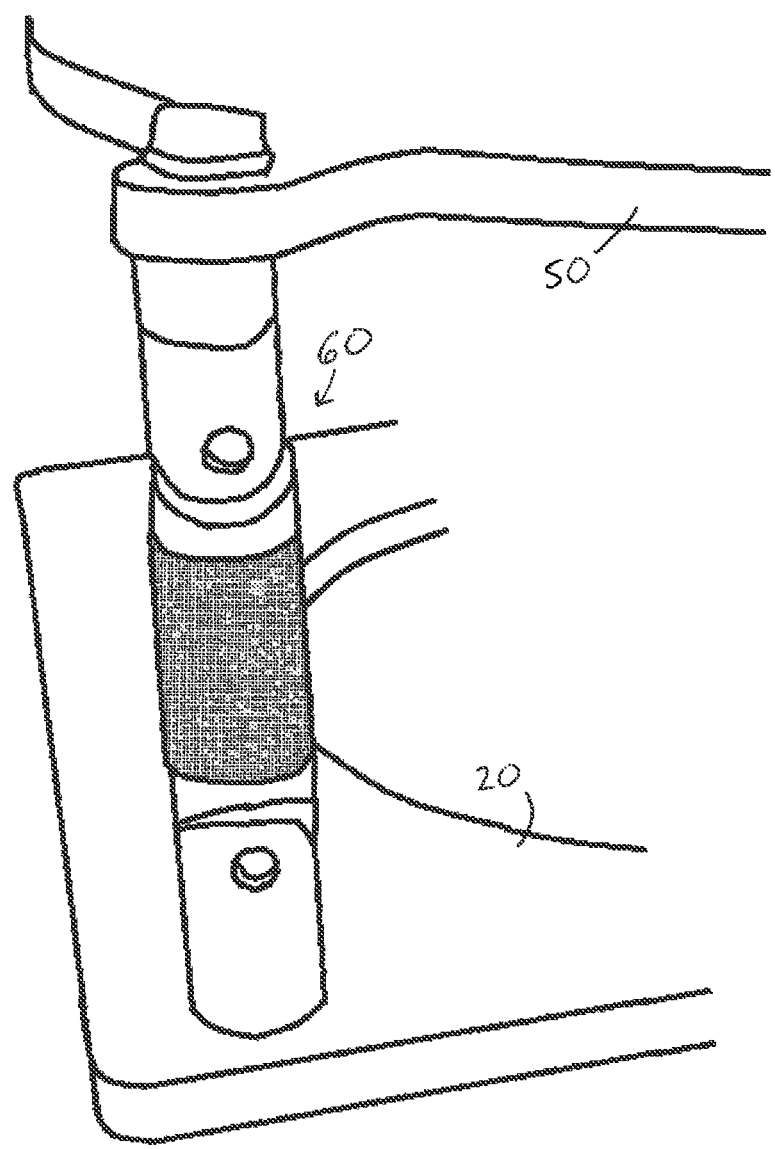
FIG. 7 is a side perspective view in partial cutaway of one of a plurality of strut members as represented in FIG. 7 and which may be operatively associated with the preferred embodiment of FIG. 1.

Additionally, disposed above the base element 20 and at least partially surrounding the ankle is a support member 50, which is depicted in FIGS. 6 and 7. With primary reference to FIG. 6, the support member 50 has a plurality of apertures 21 collectively disposed substantially along its length. The apertures are disposed and structured to facilitate the connection of fixation struts, preferably using fixation bolts, which are known to those practiced in the art and are used to effect treatment of the ankle or lower leg. The support member is preferably, at least partially curvilinear including a configuration that facilitates disposition thereof that at least partially surrounds the ankle area as represented in at least FIGS. 6 and 9-11. At least one strut aperture 51 is present on the support member 50 and extends partway or totally through the support member 50 and allows for attachment of the strut member to the support member 50. The method of attachment of the preferred embodiment and alternatives will be discussed in detail below.

Figure 8:
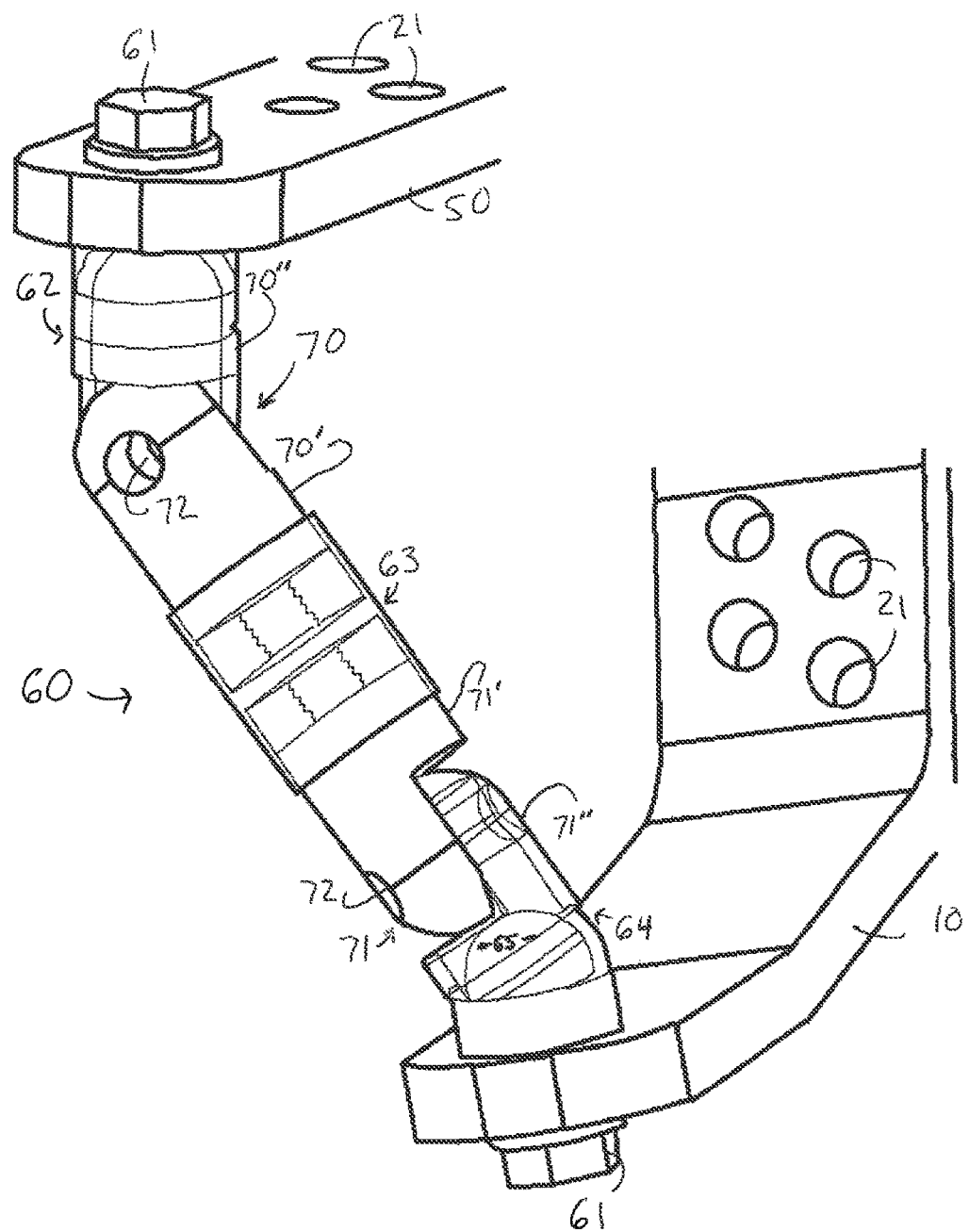
FIG. 8 is a perspective view in partial cutaway of one of a plurality of strut members as represented in FIGS. 6 and 7, with thin lines used for clarity to contrast the depiction of the internal structure of the strut member.

With primary reference to FIG. 8, a strut member 60 comprises a pair of strut attachment elements 61 that attach one end of the strut member 60 to a support member 50 and the opposing end to the side element 10 or, as shown in FIG. 7, a base element 20. With reference to FIGS. 9, 10, and 11, possible alternate embodiments of strut members are given at 60' and 60". Returning to FIG. 8, the strut attachment element 61 can be any means of fixed attachment that allows for confronting engagement between the strut member 60 and the desired attaching element, be it the aforementioned side element 10, base element 20, or support member 50 such as a threaded bolt or suitably strong adhesive substance. As depicted in at least one of the preferred embodiments, the strut attachment element 60 is comprised of a nut that fastens a threaded bolt that passes through an aperture in the desired attaching element to ensure abutment between the attaching element and the strut member 60. The strut member 60 is structured so as to facilitate the variable disposition of the support member 50, a base element 20, and/or a side element 10 relative to the ankle. The strut attachment element 61 that passes through the support member 50 is attached to a first housing 62 and abuts the support member 50. The first housing 62 can be socketed or otherwise structured to receive one end of a first hinge 70, the structure of which will be discussed in detail below. On the opposite end of the first hinge 70 is a second housing 63. The second housing 63 is socketed at either end, or can be centrally apertured, and is structured to receive one end of the first hinge 70 and one end of the second hinge 71 as depicted in FIG. 8. The end of the second hinge 71 is disposed within a third housing 64, which abuts either a base element 20 or a side element 10 in a confronting engagement facilitated by the second of two strut attachment elements 61. Further, the second housing 63 is structured to adjust or vary the length of the strut member 60 upon rotation or other appropriate manipulation thereof. Such a variance in length will be evident or accomplished by a variance of the distance between a primary first hinge member 70' and a secondary first hinge member 70".

The first hinge 70 is comprised of a primary first hinge member 70', a secondary first hinge member 70", and a hinge fastener 72. The secondary first hinge member 70" is disposed with a hollow, socket or other similar recess in the first housing 62 in such a way as to facilitate the rotary motion or disposition between the primary first hinge member 70' and the secondary first hinge member 70". The exposed end of the secondary first hinge member 70" is apertured to receive a hinge fastener 72. Abutting the secondary first hinge member 70" is the primary first hinge member 70', which is similarly apertured as shown in FIG. 8 to receive the hinge fastener 72. The abutting ends of the primary and secondary first hinge members 70' and 70" are cooperatively structured and configured to pivot about a common axis.

Additionally, one of a pair of hinge fasteners 72 joins the primary first hinge member 70' and the secondary first hinge member 70" and facilitates their rotational movement about an axis defined by the central axis of the hinge fastener 72. The hinge fastener 72 can be a bolt and nut or any similar fastening structural composition that allows for tightening to adjust the confrontation between the primary first hinge member 70' and secondary first hinge member 70". By adjusting the confrontation, it is possible to cause the first hinge 70 to become frictionally locked, which is desirable when disposing the dynamic foot plate assembly 1 into a predetermined position for treatment. When the first hinge 70 is frictionally locked, reducing the tensile forces directed along the central axis of the hinge fastener 72 will restore the ability for the primary first hinge member 70' and secondary first hinge member 70" to rotate about the aforementioned axis. The primary second hinge member 71' and the secondary second hinge member 72" are similarly attached with the second of a pair of hinge fasteners 72, the function of which is substantially the same as set forth above.

Furthermore, a second housing 63, which may be socketed on each end or else centrally apertured, is structured to receive in one end the primary first hinge member 70' and in the other end the primary second hinge member 71', as shown in FIG. 8. The second housing 63 is structured to interconnect the primary first and second hinge members 70' and 71'. The second housing 63 is further structured to facilitate the rotational movement of the primary first and second hinge members 70' and 71' relative to one another about an axis, defined as the central axis of the second housing 63.

The second hinge 71 comprises the primary second hinge member 71' and a secondary second hinge member 71" cooperatively structured and configured to pivot relative to one another about a common axis, defined as the central axis of the aforementioned hinge fastener 72 that joins the two members 71' and 71".

A third housing 64 is pivotally interconnected to the secondary second hinge member 71", is structured to facilitate an at least partially universal range of motion of the secondary second hinge member 71", and may substantially resemble of that of a ball in socket 65, as represented.

Figure 12:
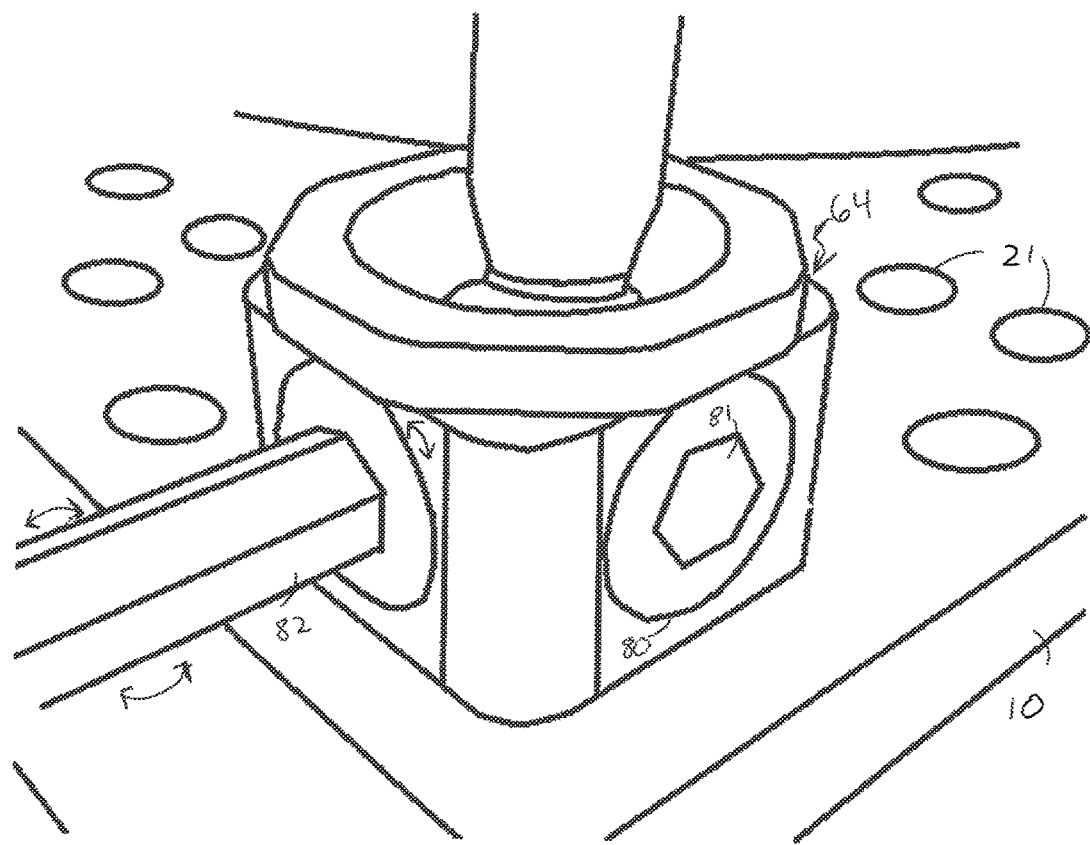
FIG. 12 is a perspective detail view in partial cutaway of one of a plurality of strut members as represented in another embodiment of the present invention.

Another embodiment of the present invention is shown in FIG. 12 and features a locking mechanism 79 providing for the disposition of the strut member 60 into a removably locked or removably fixed orientation. The locking mechanism 79 may be directly associated with the third housing 64 and comprises at least one or a plurality of, apertures structured to receive a locking bolt 80. The locking bolt 80 is coaxially aligned with the aperture of the third housing 64. The aperture in the third housing 64 is in abutting confrontation with the locking bolt 80, and such abutting confrontation is further defined by the complementary threading of the confronting surfaces of the locking bolt 80 and the third housing 64 as is common of a bolt and a nut. As a result, a rotary force upon the locking bolt 80, of the locking mechanism 79, about its central axis, which as discussed above is aligned with the central axis of the respective aperture of the third housing 64 into which the locking bolt 80 is inserted, causes the locking bolt 80 to translate along the central axis. Consequently, a rotary force, when applied to the locking bolt 80, can be made to cause the locking bolt 80 to press against the ball of the aforementioned ball and socket assembly 65, and thereby apply a frictional force sufficient to cause the ball to become frictionally locked and thus unable to move within the socket. The locking bolt 80 may itself be apertured, as at 81, configured to receive a "tool" 82, such as a hex tool, structured to provide the rotary force above described. In other embodiments, the locking bolt 80 may be structured to accommodate alternative types of tools 82, such as a Phillips screwdriver, flathead screwdriver, hex key, socket wrench, etc., to facilitate the rotary operation of the locking bolt 80.

Further, as represented in at least FIG. 11 the locking mechanism 79 may be located at opposite ends of one or more struts 60', such that the opposite ends of the one or more struts 60' may be removably fixed or locked in a predetermined orientation relative to the base 20 and or support 50 and/or side member 10. However, manipulation of the second housing 63 may still result in a variance of the length of the corresponding strut member 60' while the opposite ends thereof are in the removably fixed or locked position.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A dynamic footplate assembly structured for therapeutic use adjacent the ankle area of the body, said footplate assembly comprising:
    a base element operatively disposed adjacent a posterior portion of the ankle area,
    at least one side element dimensioned and configured to be disposed adjacent to and extend laterally along a foot portion of the ankle area,
    at least one joint movably and adjustably connecting said base element, in linear alignment, to said at least one side element,
    a support member operatively disposed in at least partially surrounding relation to the ankle area, in spaced relation above said base element and said least one side element;
    at least one strut member adjustably interconnecting said at least one side element to said support member,
    said at least one joint structured for relative, variable displacement between said at least one side element and said base element into different operative orientations relative to one another, and
    said at least one joint comprising a joint housing and a pivot element disposed and structured to independently and collectively dispose said base element and said at least one side element into said different operative orientations relative to one another.

2. The dynamic footplate assembly as recited in claim 1 wherein said at least one joint further comprises an extension element disposed in interconnecting relation between said pivot element and base element, via said joint housing.

3. The dynamic footplate assembly as recited in claim 2 wherein said extension element is interconnected to said at least one side element and movable towards and away from said base element.

4. The dynamic footplate assembly as recited in claim 2 wherein said extension element is connected to said joint housing and movable transversely to a plane of said base.

5. The dynamic footplate assembly as recited in claim 4 wherein said at least one side element is movable concurrently with said extension element and said joint housing above and below said base element relative to the ankle area.

6. The dynamic footplate assembly as recited in claim 5 wherein said joint housing and said extension element are reciprocally movable transversely to a plane of said base element to vary a height of said at least one side element relative to said base element.

7. The dynamic footplate assembly as recited in claim 2 wherein said at least one joint comprises a pivot structure rotationally interconnecting said at least one side element to said base element.

8. The dynamic footplate assembly as recited in claim 7 wherein said pivot structure comprises a ball and socket assembly disposed on both said extension element and said at least one side element, said ball and socket assembly structured for universal movement of said at least one side element relative to said base element.

9. The dynamic footplate assembly as recited in claim 2 wherein said extension element is structured to define at least one of said different operative orientations as a variable spacing between said base element and said at least one side element.

10. The dynamic footplate assembly as recited in claim 2 wherein said joint housing and said extension element are cooperatively structured to define one of said different operative orientations as a variable height spacing between said base element and said at least one side element.

11. The dynamic footplate assembly as recited in claim 2 wherein said pivot element is structured to define one of said different operative orientations as a variable angular orientation of said at least one side element relative to said base element.

12. The dynamic footplate assembly as recited in claim 1 wherein said at least one side element comprises an arch disposed adjacent said at least one joint and movable with said at least one side element into said different operative orientations.

13. The dynamic footplate assembly as recited in claim 1 further comprising at least two side elements each sized and configured to be disposed adjacent to and extend along a different side of the foot; and at least two joints each movably and adjustably connecting said base element to a different one of said side elements; each of said joints structured for variable displacement of a corresponding side element relative to said base element into different operative orientations.

14. The dynamic footplate assembly as recited in claim 13 wherein each side element comprises an arch disposed adjacent a corresponding joint and movable with a corresponding side element into said different operative orientations.

15. The dynamic footplate assembly as recited in claim 1 wherein said at least one strut member is structured to facilitate a variable orientation of said at least one side element relative to said support member.

16. The dynamic footplate assembly as recited in claim 15 further comprising a plurality of strut members adjustably interconnecting said support member to said base element and said at least one side element, said plurality of strut members structured to facilitate a variable orientation of said support member relative to said base element and said at least one side element.

17. The dynamic footplate assembly as recited in claim 16 wherein each of said plurality of strut members comprises a first hinge member, said first hinge member comprising a primary first hinge member and a secondary first hinge member, said primary first hinge member pivotally interconnected to said secondary first hinge member, said primary first hinge member rotationally interconnected to said support member.

18. The dynamic footplate assembly as recited in claim 17 wherein each of said plurality of strut members further comprises a second hinge member, said second hinge member comprising a primary second hinge member and a secondary second hinge member, said primary second hinge member pivotally interconnected to said secondary second hinge member, said primary second hinge member rotationally interconnected to a correspondingly disposed one of said base element or said at least one side element.

19. The dynamic footplate assembly as recited in claim 17 further comprising at least one lock assembly connected in removably locking engagement to said first hinge member, said at least one lock assembly structured to removably secure said first hinge member into a predetermined angular orientation.

20. The dynamic footplate assembly as recited in claim 19 further comprising a hand manipulated tool removably connected to said at least one lock assembly and operative to position said at least one lock assembly into and out of locking engagement with said first hinge member.

21. The dynamic footplate assembly as recited in claim 15 wherein said at least one strut member comprises a first hinge member and a second hinge member connected at opposite ends of said at least one strut member, a plurality of lock assemblies each connected in removably locking engagement to a different one of said first hinge member and said second hinge member, each of said lock assemblies structured to removably secure corresponding ones of said first hinge member and said second hinge member into a predetermined angular orientation.

22. The dynamic footplate assembly as recited in claim 21 further comprising a hand manipulated tool removably connectable to each of said lock assemblies and operative to independently position each of said lock assemblies into and out of locking engagement with a corresponding one of said first and second hinge members.

23. A dynamic footplate assembly structured for therapeutic use adjacent the ankle area of the body, said footplate assembly comprising:
   a base element operatively disposed adjacent a posterior portion of the ankle area,
   at least one side element adjustably connected to said base and dimensioned and configured to be disposed adjacent to and extend laterally along a foot portion of the ankle area,
   at least one joint movably and adjustably connecting said base element in linear alignment to said at least one side element,
   said at least one joint disposed and structured for relative, variable displacement of said at least one side element and said base element into different operative orientations of said linear alignment, relative to one another,
   a support member operatively disposed in partially surrounding relation to the ankle area, in spaced relation above said base element and said at least one side element;
   a plurality of strut members each comprising a first hinge member and a second hinge member connected at opposite ends thereof, and
   said first and second hinge members of said plurality of strut members adjustably interconnecting said support member to said base element and said at least one side element to which said plurality of strut members are attached.

24. The dynamic footplate assembly as recited in claim 23 further comprising at least one lock assembly connected in removably locking engagement to one of said first and second hinge members, said at least one lock assembly structured to removably secure a corresponding strut into a selected angular orientation.

25. The dynamic footplate assembly as recited in claim 24 further comprising a hand manipulated tool removably connected to said at least one lock assembly and operative to position said at least one lock assembly into and out of locking engagement with a corresponding one of said first and second hinge members.

* * * * *